United States Patent [19]

Mathies et al.

[11] Patent Number: 4,979,824
[45] Date of Patent: Dec. 25, 1990

[54] HIGH SENSITIVITY FLUORESCENT SINGLE PARTICLE AND SINGLE MOLECULE DETECTION APPARATUS AND METHOD

[75] Inventors: Richard A. Mathies; Konan Peck, both of Contra Costa County; Lubert Stryer, Santa Clara County, all of Calif.

[73] Assignee: Board of Trustees of the Leland Stanford Junior University, Stanford, Calif.

[21] Appl. No.: 358,782

[22] Filed: May 26, 1989

[51] Int. Cl.$^5$ .......................................... G01N 21/64
[52] U.S. Cl. .................................. 356/318; 356/417; 250/458.1
[58] Field of Search ................... 356/72, 73, 317, 318, 356/417; 250/458.1, 459.1, 461.1, 461.2

[56] References Cited

U.S. PATENT DOCUMENTS 4,573,796  3/1986  Martin et al. ...................... 356/318
4,793,705  12/1988  Shera ................................ 356/318

OTHER PUBLICATIONS

Hirschfeld, T., "Optical Microscopic Observation of Single Small Molecules", Dec. 1976, vol. 15, No. 12, *Applied Optics*, pp. 2965–2966.
Dovichi, Norman J.; Martin, John C.; Jett, James H.; Trkula Mitchell; Keller, Richard A., Mar. 1984, *Analytical Chemistry*, vol. 56, No. 3, pp. 348–354.
Nguyen, Dinh C.; Keller, Richard A.; Trkula Mitchell, "Ultrasensitive Laser—Induced Fluorescence Detection in Hydrodynamically Focused Flows", Feb. 1987, *J. Opt. Soc. Am. B*, vol. 4, No. 2, pp. 138–143.
Mathies A. Rschard & Stryer, Lubert, "Single—Molecule Fluorescence Detection: A Feasibility Study Using Phycoerythrin", Applications of Fluorescence in the Biomedical Sciences, pp. 129–140.
Nguyen, D. C., Keller, R. A.; Jell, J. H.; Martin, J. C., "Detection of Single Molecules of Phycoerythrin in Hydrodynamically Focused Flows by Laser—Induced Fluorescence", *Anal. Chem.*, vol. 59, No. 17, Sept. 1, 1987, pp. 2158–2161.

Primary Examiner—F. L. Evans
Attorney, Agent, or Firm—Flehr, Hohbach, Test, Albritton & Herbert

[57] ABSTRACT

Apparatus is described for ultrasensitive detection of single fluorescent particles down to the single fluorescent molecule limit in a fluid or on a substrate comprising means for illuminating a predetermined volume of the fluid or area of the substrate whereby to emit light including background light from the fluid and burst of photons from particles residing in the area. The photon burst is detected in real time to generate output representative signal. The signal is received and the burst of energy from the fluorescent particles is distinguished from the background energy to provide an indication of the number, location or concentration of the particles or molecules.

19 Claims, 4 Drawing Sheets

U.S. Patent   Dec. 25, 1990   Sheet 1 of 4   4,979,824
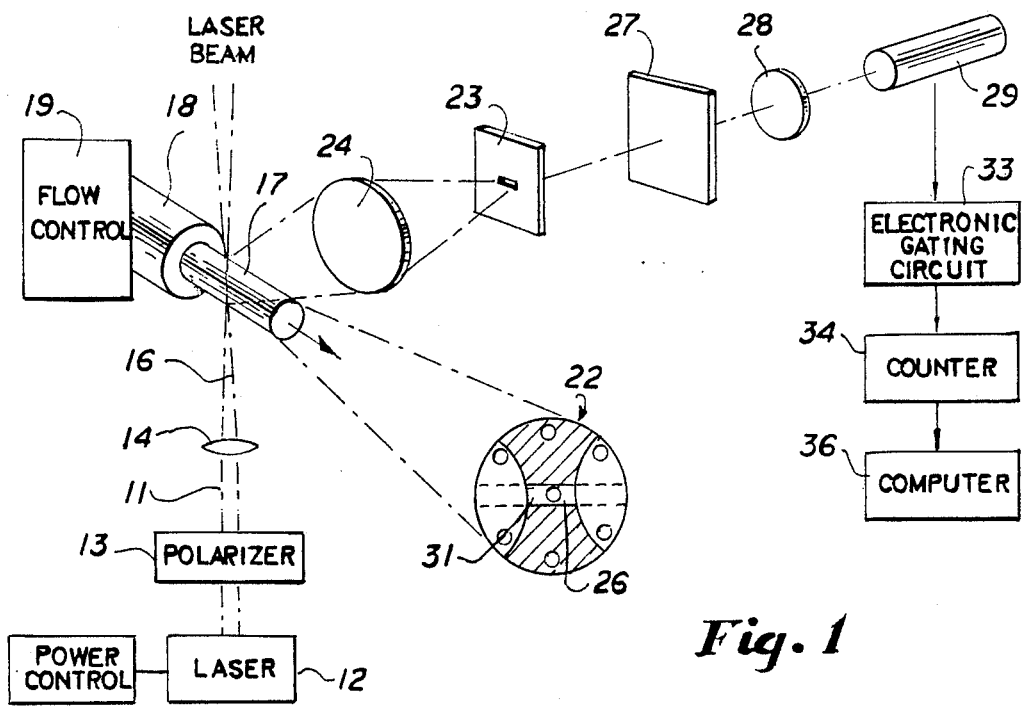
Fig. 1
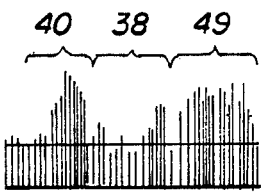
Fig. 2A
Fig. 2B
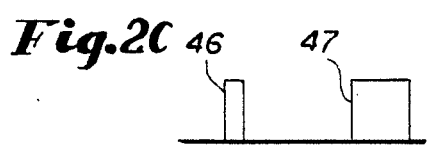
Fig. 2C
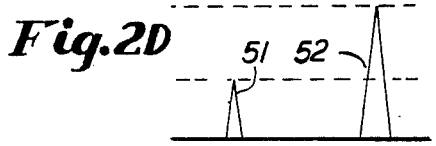
Fig. 2D
Fig. 2E
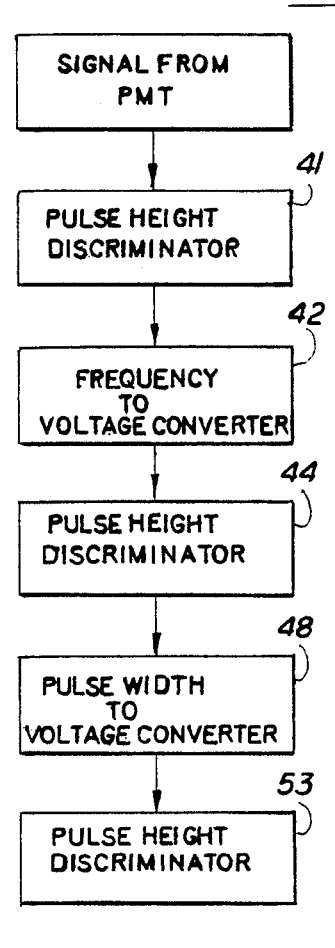
Fig. 2F
Fig. 2

HIGH SENSITIVITY FLUORESCENT SINGLE PARTICLE AND SINGLE MOLECULE DETECTION APPARATUS AND METHOD

This invention was supported in part by grants from the National Science Foundation, the National Institute of Health, and by the Director, Office of Energy Research, Office of Health and Environmental Research, Physical and Technological Research Division, of the U.S. Department of Energy.

BRIEF DESCRIPTION OF THE INVENTION

This invention relates generally to an apparatus and method for the detection of individual fluorescent particles down to the single molecule limit, and more particularly, to an apparatus and method for measuring the concentration of fluorescent particles or molecules in a fluid solution, or for locating and/or counting fluorescent particles or molecules on surfaces or in films.

BACKGROUND OF THE INVENTION

There is a need for sensitive apparatus and methods for the detection of individual molecules or particles. It is particularly important in medical and biological research to be able to measure the concentration, number or position of individual particles such as bacteria, viruses, and DNA fragments which are intrinsically fluorescent or can be labeled with fluorescent markers or probes.

In the quest for enhanced sensitivity, Hirschfeld used evanescent-wave excitation to detect an antibody molecule labeled with 80 fluoresceins adsorbed on a glass slide.[1] Using a flowing sample, Dovichi et al.[2] achieved a detection limit of 22,000 rhodamine 6G molecules in a 1 s integration time, and Nguyen et al.[3] extended this limit to 800 molecules with hydrodynamically-focused flows. Mathies and Stryer[4] pointed out the limits imposed by photodestruction and detected three molecules of B-phycoerythrin (PE) in a probe volume of 10 pL. Recently, Nguyen et al. observed bursts of fluorescence when a $10^{-12}$ M solution of PE was flowed through a focused laser beam, and they interpreted these bursts as being due to the passage of individual molecules[5]. To detect single molecule fluorescence bursts, one must ensure that the probability of observing emission from two molecules simultaneously in the beam is negligible. In the distribution function, the probability of detecting zero counts during a given time interval from the fluorescent sample should differ from that of the solvent by less than 10%. A convenient test is that the mean count rate in the sample should increase by less than 10% compared to the blank. In the experiments of Nguyen et al., the most probable count rate with PE is double that in the blank and their probability for single occupancy (0.34) gives a double occupancy probability of 0.11. This indicates that Nguyen et al. were observing bursts of fluorescence due to the simultaneous presence of two or more molecules in the imaged volume rather than the presence of single molecules.

[1] Hirschfeld, T. (1976) Appl. Optics 15, 2965–2966.
[2] Dovichi, N. J., Martin, J. C., Jett, J. H., Trkula, M. & Keller, R. A. (1984) Anal. Chem 56, 348–354.
[3] Nguyen, D., Keller, R. & Trkula, M. (1987) J. Opt. Soc. Am. 4, 138–143.
[4] Mathies, R. A. & Stryer, L. (1986) in Fluorescence in the Biological Sciences, eds. Taylor, D. L., Waggoner, A. S., Lanni, F., Murphy, R. F. & Birge, R. (Alan R. Liss, Inc., New York), 129–140.
[5] Nguyen, D. C., Keller, R. A., Jett, J. H. & Martin, J. C. (1987) Anal. Chem 59, 2158–61.

The prior art does not provide a method and apparatus which can provide rapid ultrasensitive detection and counting of fluorescent particles down to the single molecule limit, nor does the prior art provide a method for determining the optimal conditions to obtain this high detection sensitivity.

OBJECTS AND SUMMARY OF THE INVENTION

It is an object of this invention to provide an apparatus and method for the quantitative detection of individual fluorescent particles in a solution down to the level of single molecules.

It is another object of the invention to provide an apparatus for locating and counting fluorescent particles or fluorescent molecules on substrates.

It is another object of this invention to provide an apparatus and method for detecting and quantitating individual particles in a solution or on a substrate in real time.

It is a further object of this invention to provide an apparatus and method for the quantitative detection of individual, intrinsically fluorescent particles or particles tagged with fluorescent material.

It is still another object of this invention to provide an apparatus and method in which individual particles in a fluid solution are illuminated with a beam of light and the light emitted from the particles and fluid is processed to provide a particle count.

It is another object of this invention to provide an apparatus and method in which a fluid including fluorescent particles is illuminated, and fluorescence photon bursts from the particles are distinguished from background photon emission to provide an indication of particles.

The foregoing and other objects of this invention are achieved by an apparatus for detection of fluorescent particles in a fluid which includes means for illuminating a predetermined volume of the fluid whereby light is emitted, including background scattering from said fluid and bursts of light from the particles in said fluid volume and light-detection means provides an output signal, and processing means distinguishes said bursts of photon energy from particles from the background photon energy to provide a particle indication or count.

BRIEF DESCRIPTION OF THE DRAWINGS

The foregoing and other objects of this invention will be more clearly understood from the following description, taken in conjunction with the accompanying drawings, of which:

FIG. 1 is a schematic diagram of the preferred embodiment of the present apparatus in which the particles are presented in a fluid stream.

FIG. 2 is a block diagram of the electronic gating circuit of FIG. 1 showing the signal input and output at various points in the circuit.

DETAILED DESCRIPTION OF PREFERRED EMBODIMENT(S)

Figure 3:
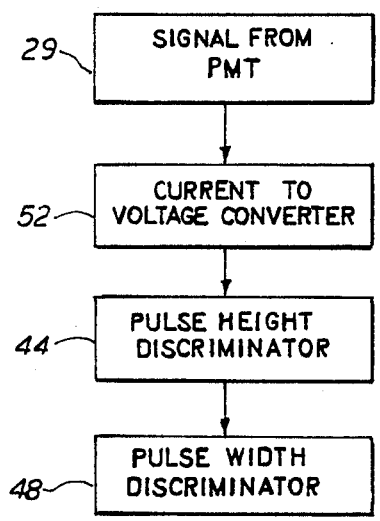
FIG. 3 is another embodiment of the gating circuit of FIG. 1.

Referring now to FIG. 1, a laser beam 11 is projected by a laser 12 through a polarizer 13 and focused by a lens 14 onto to the fluid stream as shown by the focused beam 16. The beam is focused onto flowing sample fluid stream 17 flowing in a capillary tube 18. Schematically shown is a flow control means 19 which serves to control the flow velocity of the stream 17. The laser polarization is oriented in the scattering plane by the polarizer 13 to minimize background scattering. The laser beam illuminates the area 21 shown in the enlarged view 22. An image of the illuminated volume is imaged onto a spatial filter 23 by the objective lens 24. The spatial filter 23 reduces the illuminated area and volume which is probed to the volume shown by reference number 26. The spatial filter defines the height and width of the probe volume. A spectral filter 28 rejects scattered Rayleigh and Raman emission from the illuminated volume. The energy passing spatial and spectral filters is focused by a focusing lens 28 onto a phototransducer 29 which may be a photomultiplier tube or any other type of phototransducer having the requisite sensitivity.

When a fluorescent particle 31 flows through and is irradiated by the laser beam, a burst of photons are generated. This burst of photons, together with the background emission, is detected by the photomultiplier tube which provides an output signal. This output signal is applied to an electronic gating circuit 33 which is designed to look for bursts of particular amplitude and duration. The bursts of interest have a duration equal to the transit time through the volume and at least a minimum amplitude. When such a burst is detected, the resulting signal is applied to counter 34 and to a computer 36, which can process and store the processed counts over predetermined times to provide an indication of concentration or other relevant information.

Referring to FIG. 2, the output from the photomultiplier tube is shown in FIG. 2A and is comprised of a plurality of photon bursts including both low frequency background emission 38 representing Rayleigh and Raman scattering, and high frequency bursts 39 representing a particle traveling through the probe volume, and electronic noise 40. The signal from the photomultiplier tube is supplied to a pulse height discriminator 41 which passes pulses with predetermined amplitudes and then to a frequency to voltage converter 42 which converts the frequency of pulses to a voltage 43. Thereafter, the voltage 43 is applied to a pulse height discriminator 44 which provides a pair of output pulses 46, 47 and discriminates against low frequency background emissions. A pulse-width-to-voltage converter 48 receives the pulses and provides the output shown at 51, 52, FIG. 2E.

A pulse height discriminator 53 detects the pulses 51 and 52 and provides an output pulse 54 when the pulse 52 exceeds a predetermined amplitude or lies within a predetermined range indicated by the two doted lines in FIG. 2E. A window discriminator may be employed to reject very long pulses that are not physical. The amplitude is indicative of the presence of a particle. The circuit discriminates against high frequency short duration sharp electronic spikes 40 as represented by the pulse 51 as well as low frequency background emissions 38.

An alternate method of detection is shown in FIG. 3, wherein the signal from the photomultiplier tube 29 is applied to a current-to-voltage converter 52 which will generate a signal corresponding generally to that shown in FIG. 2C. The signal can then be applied to pulse height discriminator 44 and pulse width discriminators 48 to provide an output indicative of the presence of particles.

Figure 4:
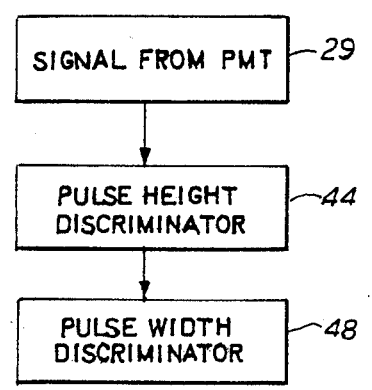
FIG. 4 shows still another embodiment of the gating circuit of FIG. 1.

FIG. 4 is a generalized block diagram of the processing circuitry which comprises the pulse height discrimination and pulse width discrimination 48 described above.

Figure 5:
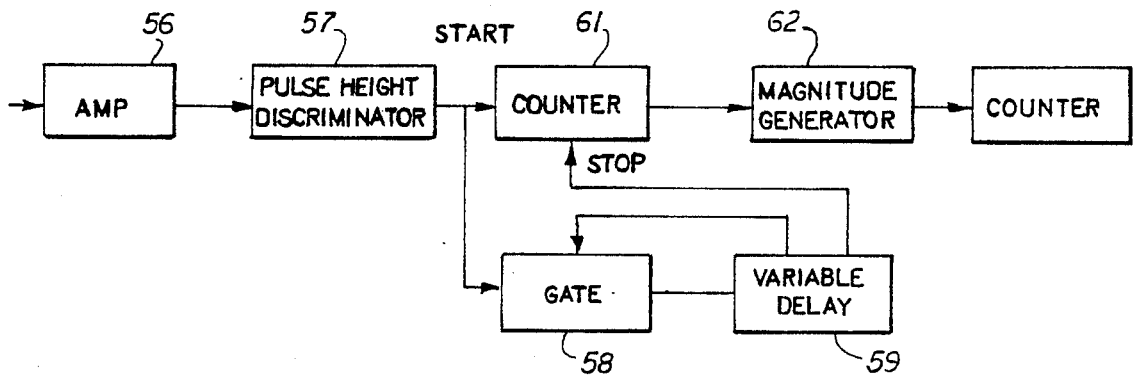
FIG. 5 shows a digital circuit embodiment of the gating circuit.

In FIG. 5, there is shown a digital circuit for performing the pulse height and pulse width discrimination to detect valid bursts of photons from fluorescent particles. The output from the photomultiplier tube is amplified 56 and applied to the pulse height discriminator 57 to give a signal of the type shown in FIG. 2B. The output of the pulse height discriminator is applied to a counter which is started by the first incoming pulse. The pulse also closes a gate 58 and starts a variable delay circuit 59 which is set to match the transit time of the molecule through the laser beam. The counter keeps counting until the variable delay circuit triggers the counter 61 to stop, reset the and counter, and opens the gate to allow a new delay cycle to start. A magnitude comparator 62 compares the number of counts which the counter generates over the delay period with a predetermined background value since the fluorescent bursts from particles have higher count rate than the background emission. If the number exceeds the predetermined background value, it is an indication of a molecule passed through the beam and one count is generated.

It is important in single particle or molecule detection to provide conditions which make the single particle or molecule event as bright as possible compared with the fluctuations in the background emission. In this regard, the laser needs to be tightly focused and the spatial filter needs to define a probe volume that is small enough to have the probability of multiple molecules or particles occupying the volume negligible. The laser power needs to be chosen to provide the brightest fluorescence without generating excessive background emission.

In order to obtain the sensitivity necessary to detect single molecules by laser-induced fluorescence, incident laser excitation intensity and the transit time of the molecules through the laser beam must be controlled. Our theory and experiments show that the saturation of the excited state absorption and photochemical photodestruction place fundamental limits on the laser power and exposure time (transit time) that will give the best signal-to-noise ratio. To define the optimal conditions, it is useful to first define the relevant variables:

(1) The observed fluorescence emission decay rate is defined as $k_f$ (in photon/sec);

(2) The rate of excitation of the molecular absorption is given by $k_a$ (in photon/sec). This rate depends on the incident light intensity and on the optical absorption cross-section of the molecule.

$$k_a = I\sigma_a \tag{1}$$

Here $\sigma_a$ is the absorption cross-section (in cm$^2$/molecule) which is related to the conventional molar extinction coefficient $\epsilon$ (in liter/(mole cm)) by $$\sigma_a = 3.824 \times 10^{-21}\epsilon \tag{2}$$

(3) The transit time of the molecule through the laser beam or the transit time of the beam over the molecule is given by $\tau_t = w/v$ (in sec) where w is the width of the laser beam and v is the velocity.

(4) The characteristic photodestruction rate $k_{pd}$ (in sec$^{-1}$) defines the first order rate at which the molecules are destroyed by light. It is related to the photodestruction quantum yield $\Phi_{pd}$ by $$k_{pd} = \Phi_{pd} k_f \tag{3}$$

The characteristic photodestruction decay time $\tau_{pd}$ is given by the reciprocal of $k_{pd}$.

Equation (4) below gives the fluorescence-per-molecule divided by the square root of the mean background-signal-per-transit time. This is a signal-to-noise ratio because we are interested in optimizing the signal (fluorescence-per-molecule) relative to the fluctuations in the background. The equation is:

$$S/\sqrt{B} \ (k\tau)^{-\frac{1}{2}}[1 - \exp\{-k\ \tau/(k+1)\}] \tag{4}$$

In this equation the variable k is defined as $k_a/k_f$ and $\tau$ is defined as $\tau t/\tau_{pd}$. Thus, the optimization of the experiment depends on the ratio of the excitation rate to the emission rate ($k_a/k_f$) and on the ratio of the transit time to the photodestruction time ($\tau_t/\tau_{pd}$). A two-dimensional plot of $S/\sqrt{B}$ as a function of k and $\tau$ is presented in FIG. 6. This is a fundamental function which applies to all fluorophores.

Figure 6:
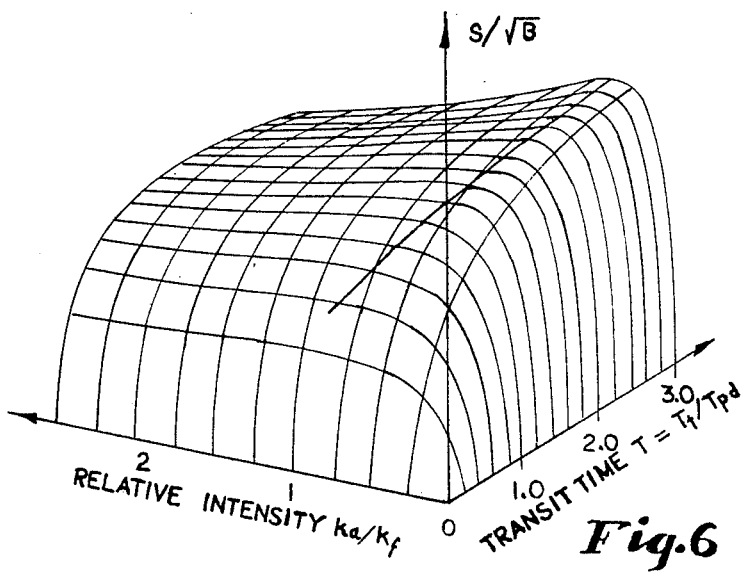
FIG. 6 shows the laser intensity and particle transit time for optimum signal-to-noise conditions.
Figure 7:
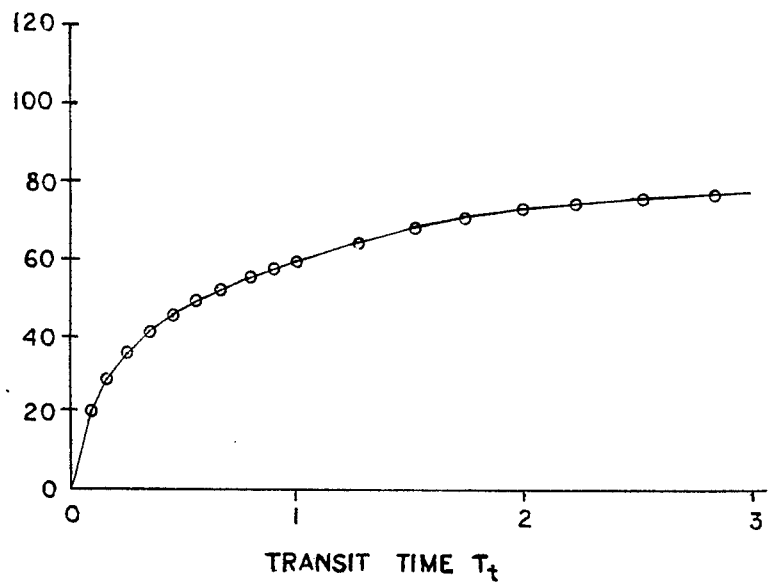
FIG. 7 is a plot of optimal signal-to-noise ratio at optimal laser intensities as a function of transit time.

To optimize the conditions for a particular fluorophore it is only necessary to know the characteristic photodestruction time and the observed fluorescence lifetime. The dots on FIG. 6 indicate the optimum $S/\sqrt{B}$ values at the optimum light intensities for transit times $\tau$ from 0 to three. FIG. 7 presents a plot of the optimal $S/\sqrt{B}$ as a function of the transit time. To perform an experiment, one simply selects the longest transit time that is practical for the experiment at hand and then selects the excitation intensity that gives maximum $S/\sqrt{B}$ at that transit time.

The apparatus of FIGS. 1 and 2 was used to detect single-molecule fluorescence in a subpicomolar solution of monomers and dimers of B-phycoerythrin (PE). Argon laser 12 provided an excitation beam which was focused to a few $\mu$m spot size at the center of a flowing sample stream 17 contained in capillary tube 18. The flow velocity was chosen to give a transit time approximately equal to the photodestruction time for PE and the laser intensity was selected to give the optimal $s/\sqrt{B}$ as indicated in FIGS. 6 and 7. Fluorescence emission was collected by a microscope objective 24 and imaged onto a spatial filter 23. The spatial filter defined the probe volume and rejected scattering and fluorescence from the capillary walls. A fluorescence interference filter 27 was used to reject Rayleigh and Raman scattering. The fluorescence was detected with a photomultiplier tube and amplifier/discriminator. The fluorescence burst detector in FIG. 2 was then used to record the number of events in an on-line real time fashion.

Figure 8A:
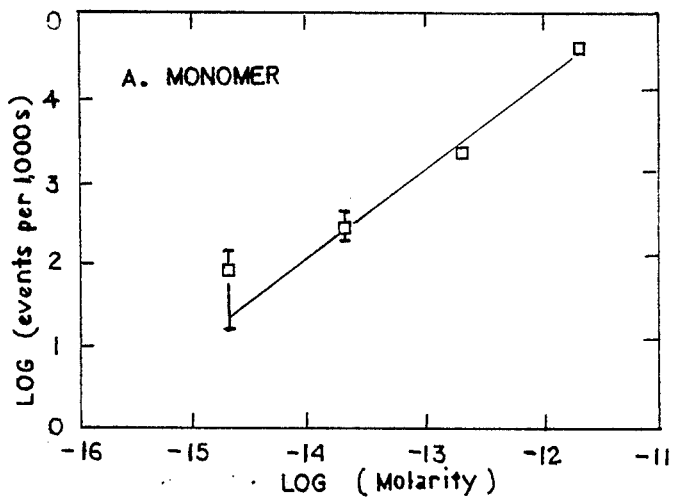
FIG. 8 is a plot showing the results of operation of the apparatus of FIG. 1.
Figure 8B:
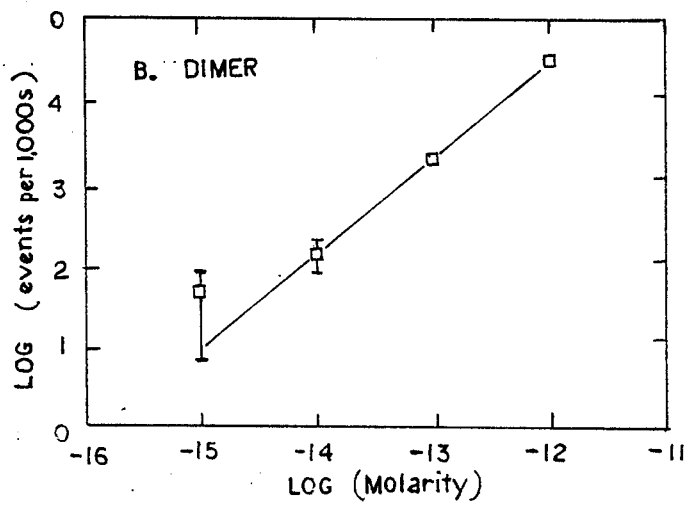

FIG. 8 presents the log of the number of single molecule events versus the log of the concentration of PE monomers and dimers.

The regression lines of these two plots have a slope fairly close to one, 1.05 for the monomer data and 1.15 for the dimer data. The linear concentration dependence proves that we are seeing single-molecule events. The dynamic range is limited by sampling time at low concentrations and by multiple occupancy at high concentrations. Higher than $10^{-12}$ M, the mean will shift up due to the fluorescence around the probe volume. These experiments were all performed at a sufficiently low concentration so that the probability for single occupancy was less than approximately 0.02. This further ensures that we are seeing single molecule events.

In FIG. 1 the fluid solution flows through the illuminated area whereby particles emit a burst of photons as they are in the volume. It is apparent that the illuminated areas may be moved over a surface or film on a substrate to locate and detect particles. The end effect is the same since the particles emit only for the transit time $\tau$ during which they are illuminated. By moving the light beam relative to the surface or by moving the substrate such as on a slide or the like relative to the light beam, it is possible to scan the total area contained on the substrate or slide to locate or count particles.

Figure 9:
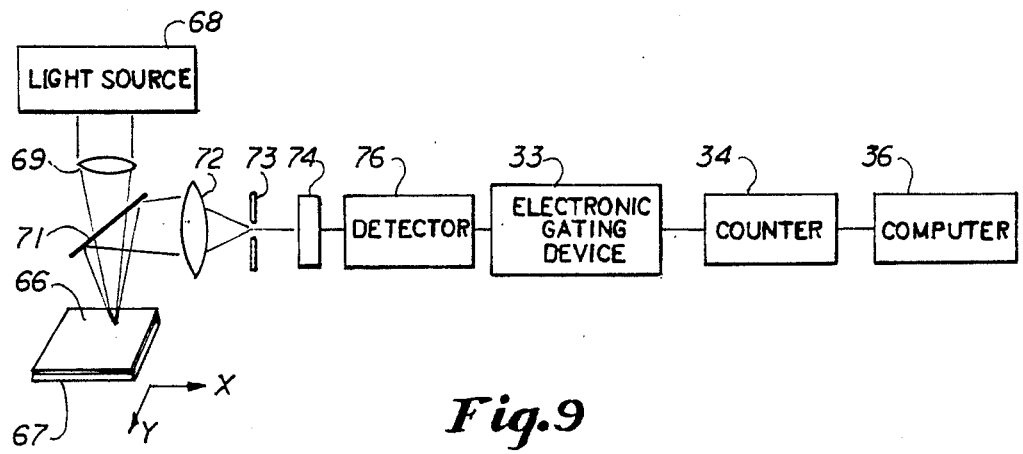
FIG. 9 is a schematic block diagram of another embodiment of this invention for counting and locating fluorescent particles or molecules on a substrate.

Referring to FIG. 9, the solution can be carried on a substrate or a slide 67 as a thin film 66, in filter paper or in a gel which can be moved by suitable X-Y drive means such as rack and pinions, stepper motors or the like. Light from a light source 68, which may be a laser or the like, is focused onto the slide by a lens 69. The light passes through a beam-splitter 71 and impinges upon the sample solution. The photons emitted by the solution are reflected by the dichroic beam-splitter to the collection optics 72, spatial filter 73, spectral filter 74 and detector 76. As described above the spatial filter defines the area which is being viewed and the spectral filter rejects scattered Rayleigh and Raman emissions. The signal is then processed by gating circuit 33, counted by counter 34 and applied to the computer at 36 as previously described. Thus this provides a fluorescent single particle scanner for use in connection with a slide or the like. By controlling the X-Y drive the total film may be analyzed. The transit time $\tau$ of the particles in the illuminated volume is controlled by the speed of movement of the stages. The area can be scanned as desired. Any of the signal processing electronic circuits described above can be employed to process the output of the detector and provides a particle identification output.

Figure 10:
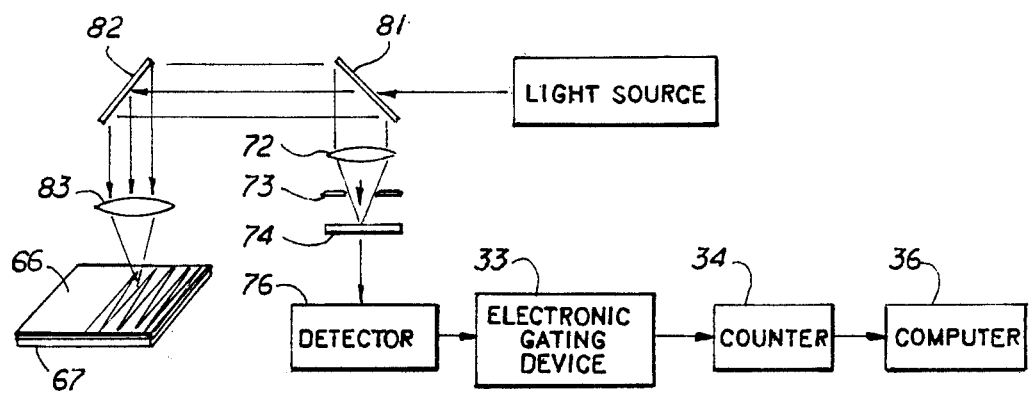
FIG. 10 is a schematic diagram of still another embodiment of this invention for counting and locating fluorescent particles or molecules on a substrate.

FIG. 10 shows another apparatus for scanning film 66 on a substrate 67. Rather than translating and moving the substrate, the substrate is stationary and the projected beam is scanned by a scanning mirror or assembly. Referring to FIG. 10, a light source 78 projects a light beam 79 which passes through the dichroic beam-splitter 81 and is deflected by scanning mirror assembly 82 and focused by scan lens 83 onto the film 66. The emitted photon energy is collected by the scan lens deflected by the scanning mirror assembly to a beam-splitter 81 where it impinges upon the focusing and collecting optics 72, passes through the spatial filter 73, spectral filter 74 and is collected by a detector 76. The output then analyzed by the electronic gating device 33, counter 34, and then to computer 36. The scanning mirror may comprise two scanning galvanometer mirrors which are deflected with signals applied to the galvanometer motors to deflect the mirrors. One mirror is moved rapidly in a first direction to scan across the sample and a second mirror with slower rate to advance the scan provides a raster scan of the type illustrated by the lines 84. Alternatively, the beam can be scanned slowly in the x-direction by a stepper motor or the like. Again the electronic currents associated with the detector provide the necessary signal discrimination to identify and detect single particles.

Figure 11:
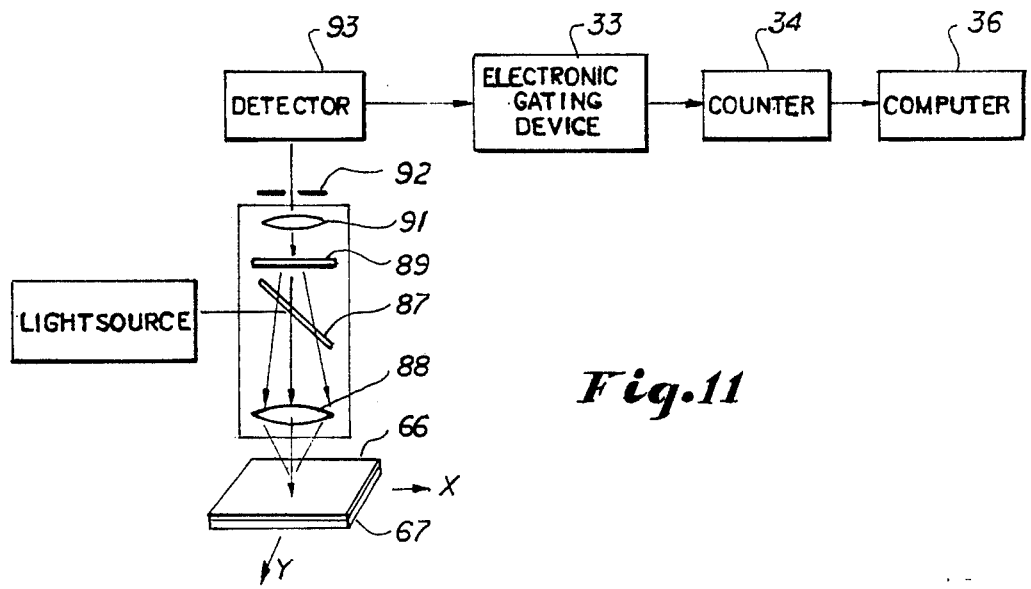
FIG. 11 is a schematic diagram of a further embodiment of this invention for counting and locating fluorescent particles or molecules on a substrate.

In FIG. 11 the substrate 67 and film 66 are placed on a translation stage of the type described with reference to FIG. 9. A light source 86 which provides energy to a dichroic beam-splitter 87, and the energy is focused by the lens 88 onto the film 66. The emitted energy is picked up by the lens 88, passed through the dichroic beam-splitter 87 through a spectral filter 89, focusing lens 91 and spatial filter 92 to the detector 93. The output signal from the detector is processed by the electronic circuit comprising electronic gating device 33, counter 34, and computer 36.

It is apparent that in each of the above examples the electronic and gating is based upon the fact that when a fluorescent molecule or particle is transiting through the illuminated volume either by motion of the particle or motion of the illuminated area, it is illuminated for a predetermined period of time and emits a burst of photons. This burst of photons can be distinguished from background emission by using the single particle burst detector of the present invention which responds to only when the photon bursts have the proper magnitude and duration or width.

While this invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. An apparatus for detection of single fluorescent particles and/or molecules in a fluid which comprises:
    means for illuminating a predetermined volume of the fluid;
    means for causing particles to transit through said illuminated volume whereby fluorescent energy emitted from said volume responsive to the illumination includes background energy and bursts of energy from particles or molecules as they transit through said volume;
    means for detecting said energy and providing an output signal; and
    means for receiving said output signal and distinguishing bursts of energy from said particles from background energy or electronic noise and providing an indication of the detection of a particle or molecule transiting through said volume.

2. Apparatus as in claim 1 wherein said means for receiving and distinguishing particle bursts of energy comprises means for detecting the amplitude and duration of said bursts.

3. Apparatus as in claim 2 in which said means for detecting the amplitude and duration of said burst comprises a frequency to voltage converter which produces an analog signal, a pulse height discriminator for receiving said analog signal and providing output pulses having a pulse width equal to the time which the signal exceeds a predetermined value and a pulse width discriminator providing an output when the pulse width exceeds a predetermined value indicative of the transit time of a particle.

4. Apparatus as in claim 3 in which said pulse width discriminator includes a pulse width to voltage converter for receiving said output pulses and providing an output voltage having an amplitude dependent upon pulse width and a pulse height discriminator for detecting when the output voltage exceeds a predetermined amplitude or lies within a predetermined window.

5. Apparatus as in claim 2 in which said means for detecting the amplitude and duration of said bursts comprises a current to voltage converter for receiving the output of said detecting means and providing an analog output signal, a pulse height discriminator for receiving said analog signal and providing output pulses having a pulse width equal to the time said signal exceeds a predetermined value and a pulse width discriminator providing an output signal when the output pulse width exceeds a predetermined value or lies in a predetermined window or range indicative of the transit time of a particle through said volume.

6. Apparatus as in claim 2 in which said means for detecting the amplitude and duration of said bursts comprises means for counting photons which are emitted over predetermined periods and providing an output signal indicative of a particle when the count exceeds a predetermined count.

7. An apparatus according to claim 2 wherein said means for illuminating a predetermined volume of the fluid is composed of a laser.

8. Apparatus as in claim 2 wherein said means for detecting and identifying particle bursts of energy operates in real time.

9. An apparatus for detecting single fluorescent particles in a fluid comprising means for illuminating an area of said fluid to cause the fluid to emit photon energy including energy scattered from said fluid and energy from fluorescent particles in said fluid,
    means for causing fluorescent particles to transit through said area whereby said particles emit bursts of energy having a duration equal to their transit time through said area,
    lens for receiving and focusing said energy,
    a detector for receiving said focused energy and providing an output signal,
    a spatial filter interposed between said detector and lens means to define the area from which energy is received, and
    means for receiving the output signal and distinguishing bursts of photon energy emitted by said particles from background energy to provide an indication of the detection of a particle transiting said area.

10. Apparatus as in claim 9 in which said means for causing fluorescent particles to transit said area comprises means for moving the particles and fluid through said area.

11. Apparatus as in claim 10 in which said means for moving the particles and fluid through said area comprises a fluid stream.

12. Apparatus as in claim 10 in which said means for moving the particles and fluid through said area comprises placing the fluid on a stage and moving the stage relative to said area whereby to scan the fluid.

13. Apparatus as in claim 9 in which said means for causing the fluorescent particles to transit said area comprises placing the fluid on a stage and scanning the illumination over said stage.

14. Apparatus as in claim 13 in which the illumination is scanned in the X and Y direction by rotating mirrors.

15. An apparatus according to claim 13 further comprising a fluorescence microscope which focuses light on the sample through an objective lens and collects light from the sample through the same lens.

16. The method of detecting single fluorescent particles in a fluid comprising the steps of
    illuminating a predetermined volume of the fluid,
    transiting particles through said illuminated volume whereby to cause fluorescent energy to emit from said volume which includes background energy and bursts of energy from the transiting particles, and
    processing said emitted energy to distinguish said bursts of energy from the background energy to provide an indication of particles transiting through said volume 17. The method of claim 16 in which said processing steps includes
    detecting said emitted energy and generating representative electrical signals and
    processing said representative electrical signals to reject electrical signals representative of background energy and providing an output when electrical signals having amplitude and duration corresponding to the transit of particles through said volume.

18. The method as in claim 16 including the steps of choosing the illuminating energy and the transit time of the particles through the predetermined volume to provide the optimal ratio of emitted energy from particles with respect to background energy or energy fluctuation.

19. The method of claim 18 in which said steps include employing fluorescence emission lifetime and fluorescence photodestruction time of fluorophores as determining factors.

* * * * *

UNITED STATES PATENT AND TRADEMARK OFFICE
CERTIFICATE OF CORRECTION

PATENT NO. : 4,979,824

DATED : December 25, 1990

INVENTOR(S) : Richard A. Mathies, et al.

It is certified that error appears in the above-identified patent and that said Letters Patent is hereby corrected as shown below:

Column 1, line 4, below the title, insert:

--This invention was made with Government support under Contract No. GM24032 awarded by the National Institutes of Health. The Government has certain rights in this invention.--

Signed and Sealed this

Twenty-eight Day of February, 1995

Attest:

BRUCE LEHMAN

Attesting Officer

Commissioner of Patents and Trademarks